US005297557A

United States Patent [19]
Reichl

[11] Patent Number: 5,297,557
[45] Date of Patent: Mar. 29, 1994

[54] STRESS TEST SYSTEM WITH BIDIRECTIONAL FILTER

[75] Inventor: Philip Reichl, Irvine, Calif.

[73] Assignee: Del Mar Avionics, Irvine, Calif.

[21] Appl. No.: 960,959

[22] Filed: Oct. 14, 1992

[51] Int. Cl.$^5$ .............................................. A61B 5/04
[52] U.S. Cl. ................................................... 128/707
[58] Field of Search .................................. 128/702-707

[56] References Cited

U.S. PATENT DOCUMENTS

| | | | |
|---|---|---|---|
| 3,395,698 | 8/1968 | Morehouse | 128/707 |
| 4,422,459 | 12/1983 | Simson | 128/702 |
| 4,799,493 | 1/1989 | Dufault | 128/705 |
| 4,898,182 | 2/1990 | Hawkins | 128/707 |
| 5,117,833 | 1/1992 | Albert et al. | 128/702 |

Primary Examiner—William E. Kamm
Attorney, Agent, or Firm—J. D. Leimbach

[57] ABSTRACT

A system for filtering stochastic signals as embodied in stress test systems for measuring electrocardiographic (ECG) activity in response to exercise employs a bidirectional Infinite Impulse Response (IIR) filtering process over a predetermined window on a digitized version of an ECG signal to eliminate noise up to the 0.67 Hz frequency range. To eliminate phase shifting distortion in the ECG signal, the IIR filter is applied in a first direction over a predetermined window of the ECG and then applied in a second direction opposite the first direction segment over the identical window. In this manner the phase shift distortion normally associated with IIR filters is completely eliminated and superior bandwidth (as compared to FIR filters) is obtained. The response is achieved fast enough to be used in real time purpose.

14 Claims, 18 Drawing Sheets

STRESS TEST SYSTEM WITH BIDIRECTIONAL FILTER

BACKGROUND OF THE INVENTION

1. FIELD OF THE INVENTION

This invention relates to the field of filters for stochastic processes, and more specifically, to stress test systems and reducing baseline noise in electrocardiographic (ECG) signals by filtering techniques.

2. DESCRIPTION OF THE PRIOR ART

Random, or stochastic, noise is a problem that exists in many electrical and electronic signals. Distortion within the baseline of an ECG signal caused by such random noise is an existing problem in analyzing electrocardiograms. Numerous publications have dealt with the low frequency cutoff requirements of ECG signals. Recent recommendations of Ad Hoc Writing Group of the Committee on Electrocardiography and Cardiac Electrophysiology of the Council on Clinical Cardiology of the American Heart Association states that the low frequency cutoff should be on the order of 0.67 Hz provided that the filter meets certain phase and amplitude requirements.

Various techniques have been employed to reduce base line distortion in electrocardiographic (ECG) signals. The most common technique presently used is Cubic-Spline interpolation where the onset of QRS signals are isolated and interpolation techniques are employed to determine the smoothest curve joining several QRS onsets. The ECG baseline can then be estimated by subtracting the curve representing the baseline wander as estimated by the Cubic-Spline technique from the recorded ECG signal. However, the QRS onset points used by the Cubic-Spline method, do not sufficiently model noise in an ECG baseline due to the scarcity of interpolation points at low heart rates. Determination of the QRS onset can be difficult or impossible in the presence of high amplitude baseline wander. Furthermore, it is necessary to delay the ECG in order to obtain reference points (QRS onset points) for calculation of the cubic spine curve. This delay (often as long as 5 seconds or longer) renders the cubic spline interpolation unsuitable for real time monitoring of patients.

A faster method of correcting baseline distortion has been to use high pass filtering techniques. One such filtering technique is to employ Finite Impulse Response (FIR) filters, where the output is taken after the FIR transfer is combined with a delay based on an integral number of the filter. These filters offer a linear phase response providing an undistorted ECG signal. FIR filters have the disadvantage of being highly computational. Nearly ideal filter characteristics may be obtained at the price of having to perform many floating point calculations and additions.

A commonly used FIR filter is the Comb Filter. The Comb Filter is a recursive implementation of a nonrecursive FIR filter While offering the advantage of significantly lower computational requirements, this filter offers only moderate attenuation of baseline noise. The maximum stop band attenuation of the Comb Filter is a modest −13.5 db. Another disadvantage of this type of filter is that it has a wide pass band to stop band transition in the frequency domain resulting in poor noise attenuation near the cutoff frequency.

High pass Infinite Impulse Response (IIR) filters are recursive filters that offer the advantage of fewer computation than FIR filters. A problem that results from using high pass IIR filters is the unacceptable level of phase distortion that takes place within the ECG signal. This phase distortion is caused by the nonlinear phase response of IIR filters. A nonlinear phase response results in different frequency components of the signal being delayed or shifted in time by different degrees. For the class of filters appropriate to ECG filtering (Butterworth filters, because of their maximally flat frequency response) the worst distortion occurs at the cutoff frequency of the filter. This results in frequency components just above the cutoff frequency also being distorted. A solution to the phase distortion problem is to apply the IIR filter to the ECG signal in both directions. This is referred to as a zero phase IIR filter. In a forward direction, using a zero phase IIR filter, the ECG baseline distortions are filtered out but the ECG signal itself is distorted. The reverse direction filtering process corrects the distortion of the ECG signal and further attenuates baseline noise. While correcting phase distortion problems, delay problems make real time implementation of the zero phase IIR filter difficult. Therefore, implementation of a zero phase IIR filter in the exercise stress testing environment is not easily realized because signals must be analyzed and displayed in real time.

As can be seen by the foregoing discussion, there remains a need within the prior art for a filter that has a response that enables it to be useful for realtime applications, while, capable of attenuating frequencies in the 0.67 Hz range or higher without causing phase distortion problems.

SUMMARY OF THE INVENTION

The present invention follows the discovery of a method and apparatus for filtering stochastic noise from an electrical signal. The preferred embodiment disclosed is a stress test system in which an Infinite Impulse Response (IIR) filter is used to correct for baseline wander within an electrocardiographic (ECG) signal. By filtering an ECG signal in a forward direction over a selected window and then filtering the same window in a reverse direction to remove phase distortion, the present invention discloses a filter that is effective in achieving 0.67 Hz passband frequencies on ECG signals. Moreover, delays associated with the filter are small enough to enable the implementation of the filter within systems intended to be used for real time purposes. A segmented window is created and a bidirectional filter is applied to the digital data defined by the window boundaries. By employing a sufficiently short window a reduction in delay over conventional methods yields a filter that can be implemented in real time systems to eliminate phase distortion. Two basic filter variations are disclosed that are implementations of analog Butterworth filters. The Butterworth filter was selected because of its maximally flat frequency response in the pass band. Both a 3 pole and a 5 pole filter are considered. These two filters offer a trade-off between computational complexity, stop band attenuation, phase response and transient settling time.

Although a Butterworth filter provides the best compromise filter design, the present invention is not limited thereto, and moreover, designs implementing filters within fewer or greater number of poles are also applicable. Other filters, such as Bessel Filters, may be used in place of the design employing the Butterworth filter.

The Bessel filter has the advantage of providing a design containing less overshoot in response to impulse signals and the disadvantage of providing less attenuation in the stop band.

BRIEF DESCRIPTION OF THE DRAWINGS

FIG. 4b illustrates a continuation of the data flow of FIG. 4a.

DESCRIPTION OF THE PREFERRED EMBODIMENT

A filtering method and apparatus has been discovered that is useful in eliminating stochastic noise within well defined frequency ranges of an electrical signal. A specific application in stress testing is disclosed herein as the best mode known to the inventor. The preferred embodiment disclosed is a stress test system in which an Infinite Impulse Response (IIR) filter is used to correct for baseline wander within an electrocardiographic (ECG) signal. By filtering an ECG signal in a forward direction over a selected window and then filtering the same window in a reverse direction to remove phase distortion, the present invention discloses a filter that is effective in achieving 0.67 Hz passband frequencies on ECG signals. Moreover, delays associated with the filter are small enough to enable the implementation of the filter within systems intended to be used for real time purposes. A segmented window is created and a bidirectional filter is applied to the digital data defined by the window boundaries. By employing a sufficiently short window a reduction in delay over conventional methods yields a filter that can be implemented in real time systems to eliminate phase distortion.

Figure 1:
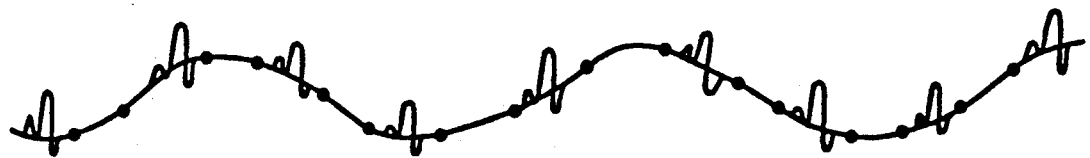
FIG. 1 is an illustration of the Cubic-Spline interpolation technique for establishing an ECG baseline.
Figure 2:
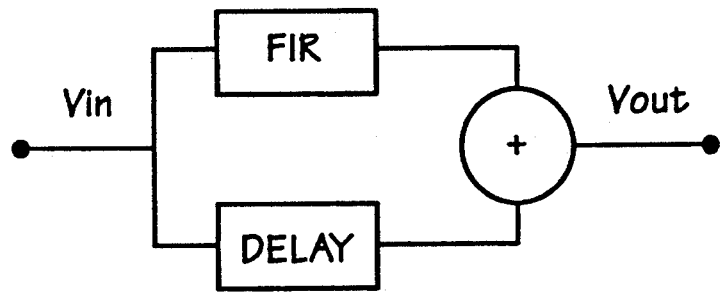
FIG. 2 is a block level diagram of a Finite Impulse Response filter.

Correcting (by filtering) the baseline of a recorded electrocardiographic signals is an important requirement in stress testing systems. By filtering electrocardiographic (ECG) signals in real time during exercise testing, significant noise components can be eliminated from the ECG baseline. This can be effectively accomplished by employing a bidirectional Infinite Impulse Response (IIR) filter over selected windows. The filtering technique consists of the application an Infinite Impulse Response (IIR) to provide a sharper pass band to stop band transition and greater stop band attenuation than the Finite Impulse Response (FIR) filters known to the art as seen in FIG. 2, and better ECG baseline noise elimination achievable using the Cubic-Spline Interpolation techniques as seen in FIG. 1.

Figure 3:
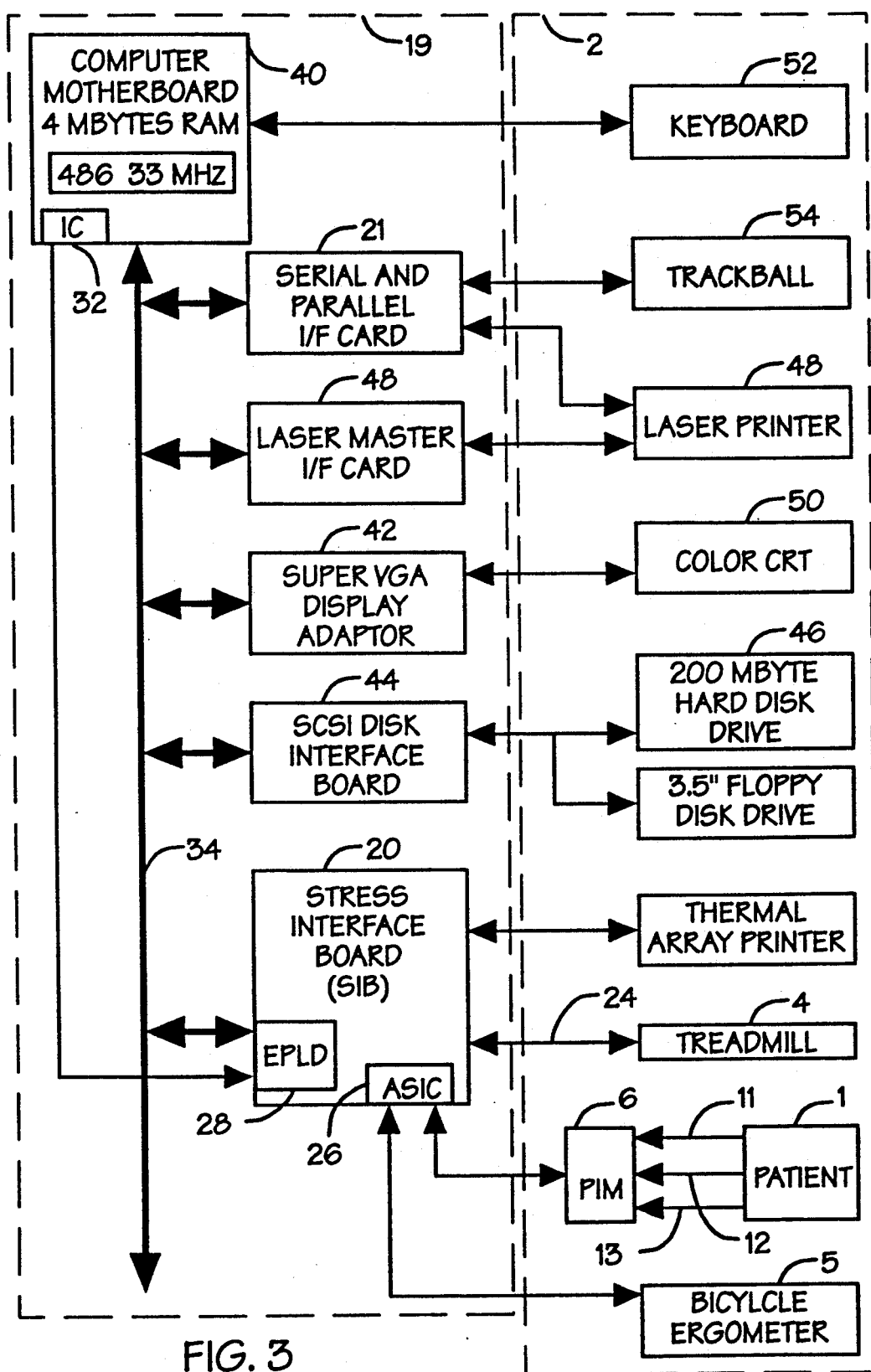
FIG. 3 is a block diagram of the stress test system used in the preferred embodiment.

Referring now to FIG. 3, which is a block level diagram of the preferred embodiment of the present invention, the entire exercise stress test system 2 consists of treadmill 4 and cart assembly 10. Treadmill 4 provides the means by which patient 1 is exercised thereby providing stress to the patient's heart. The are numerous types of stress means that could be used within the scope of the present invention. Basically these stress means are readily available and obvious substitutions such as bicycle ergometers 5 is shown in FIG. 3. Other possible substitutions, such as stairclimbers or rowing machines, and the like, are not shown. Electrodes 11, 12, and 13 are connected to patient 1 to detect bioelectric signals generated from the patient's heart. An analog electrical current is generated from electrodes 11, 12 and 13 which is sent to Patient Input Module (PIM) 6, which is worn by the patient, where it is converted to a digital signal by the PIM 6. The digital signal from PIM 6 is then is sent to the cart assembly 10 of stress test system 2. It is preferred that the analog signal from electrodes 11, 12, and 13 be converted into a digital format as soon as possible thereby preventing signal loss and introduction of noise over a longer conductor. Accordingly, the patient wears PIM 6 thus reducing the distance from electrodes 11, 12, and 13 to the point of digital conversion. The digitally converted signal created by PIM 6 is serially transmitted to the stress testing system where it is stored so that CPU 40 can perform algorithms on the data, these algorithms will be discussed in more detail below.

The remaining basic components of the stress test system consists of CRT 50, laser printer 48, a keyboard 52, trackball 54 and isolation transformer 56. Computer 19 interfaces with peripheral very commonly found within computer workstations. These peripherals are generally operated under the control of CPU board 40, consist of SCSI controller board 44, VGA display controller board 42, CRT 50, hard disc 46, laser printer interface board (hereinafter referred as the "Lasermaster") 48 Serial/Parallel interface board 21 and stress interface board (SIB) 20.

Serial data is output from PIM 6 to the computer 19 of the stress test system 2 through Stress Interface Board (SIB) 20 within computer 19 receives the serial data generated by PIM 6. The serial data are transmitted by PIM 6 along with clock, power and ground signals are transmitted by PIM 6 on separate conductors to SIB 20 where they these signals are used by the computer 19 of stress test system 2. The serial data are converted into a parallel format by SIB 20 which also synchronizes the parallel data with clock signals received by SIB 20. The serial data are converted into parallel data by ASIC device 26 which performs the function of a receiver gate array and takes the data and clock from the data/clock interface 22 and converts the serial data into 16 bit parallel words. These 16 bit parallel words are next sent to EPLD device 28 which is an interface circuit between the computer bus 34 and ASIC device 26. EPLD device will interface with the computer 19 to determine the exact times at which data is placed on computer bus 34. SIB 20 has an interface to the treadmill stress system via RS232 interface 24 which exchanges data with treadmill 4 via a serial interface. Patient data 22 within ASIC device 26, and treadmill data are sent to the CPU 40 across computer bus 34 under interrupt control; by interrupt controller 32.

Figure 4A:
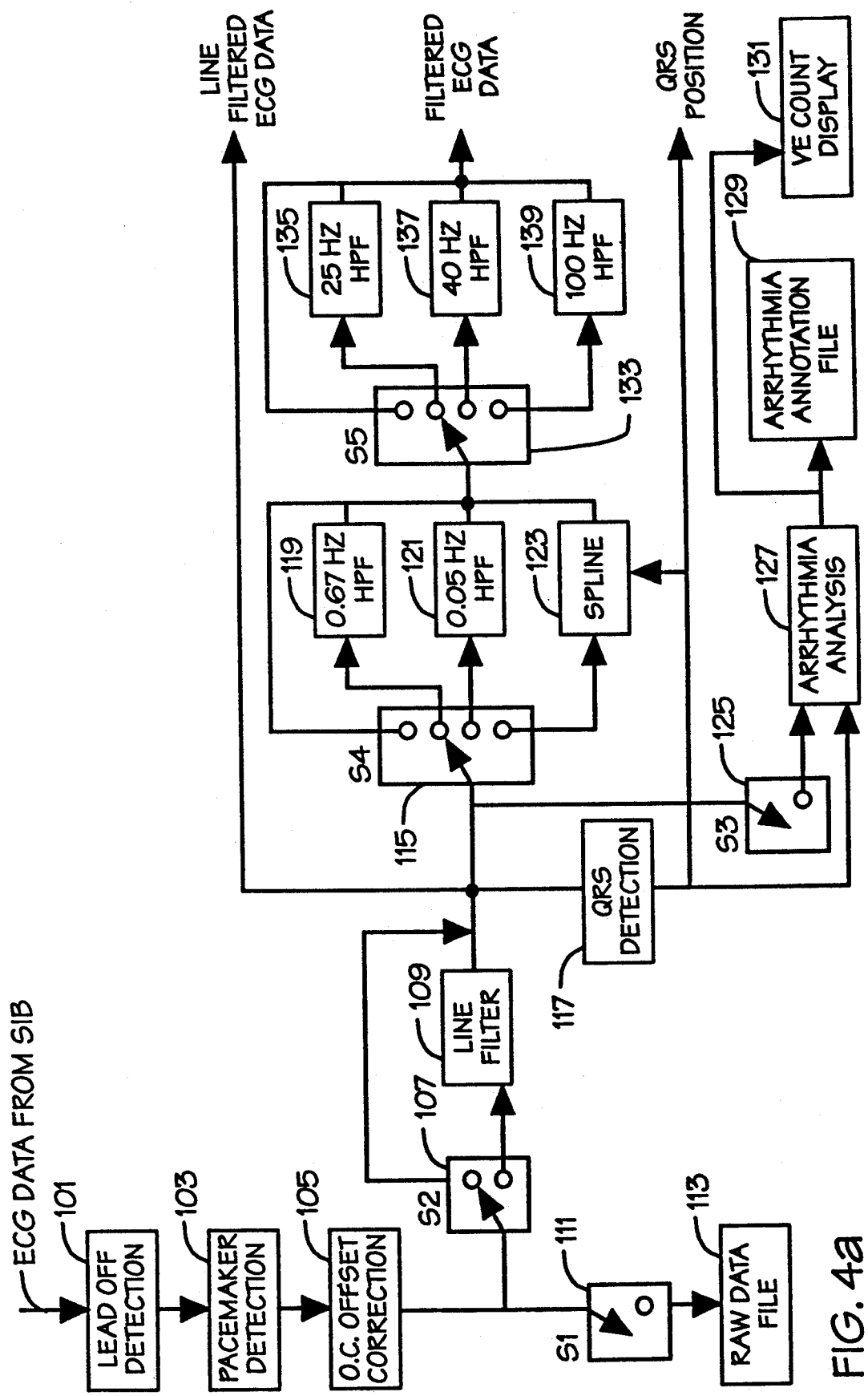
FIG. 4a illustrates data flow within the computational portion of the stress test system.
Figure 4B:
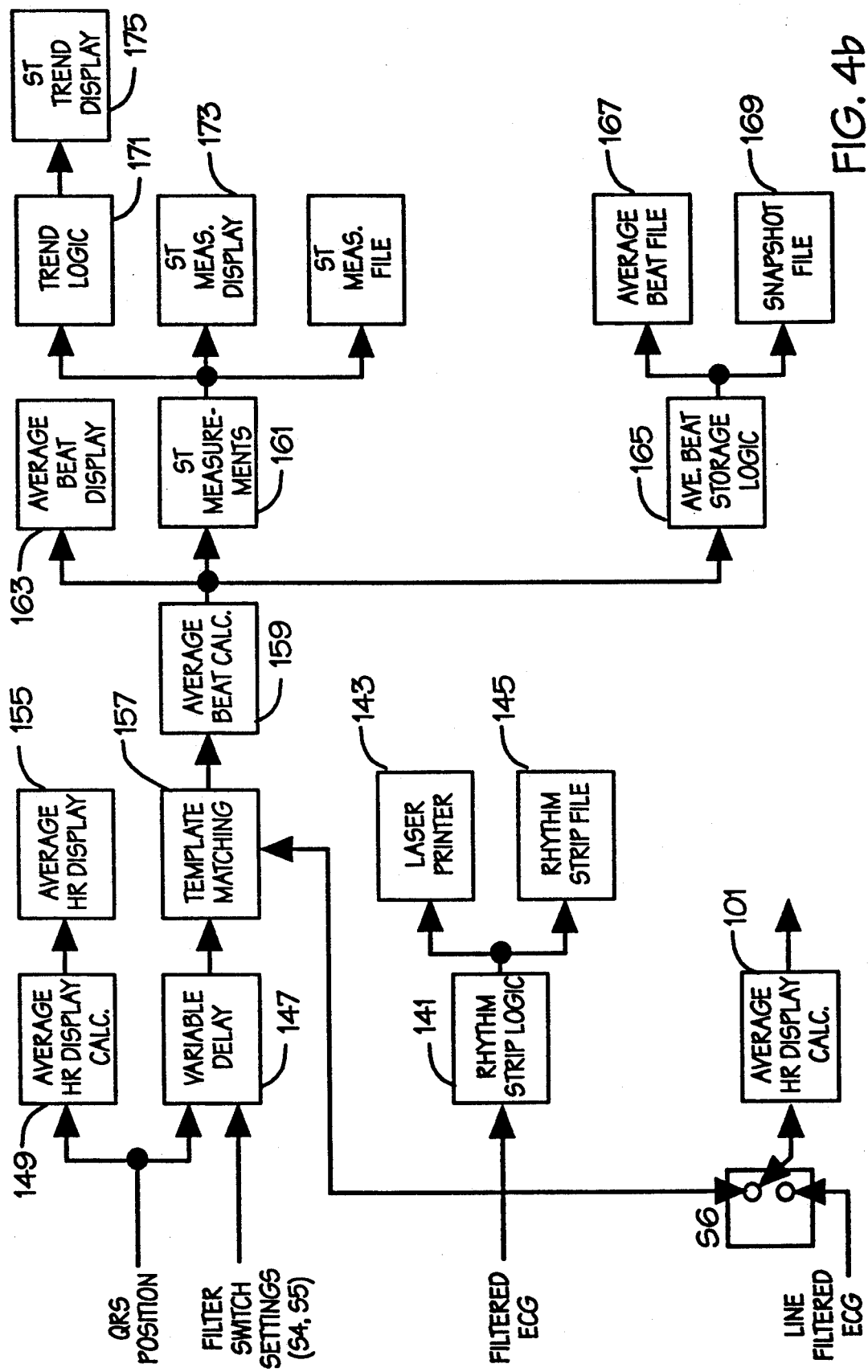

Referring now FIG. 4a and FIG. 4b as seen in conjunction with FIG. 3, illustrates the data flow throughout the various operations performed on ECG data from electrode 11, 12 and 13 input through the completion of stress test analysis. ECG data is received from SIB 20 and stored in by memory where the CPU 40 can retrieve data to perform operations on it. Lead off detection 101 is first performed on the ECG to detect instances where any of the sensing electrodes 11, 12, 13 have become dislodged from patient 1. Pacemaker Detection 103 is then performed to detect pacemaker signals generated by those patients who have pacemaker implant devices. D.C. Offset Correction 105 is performed to remove D C. components from the ECG signal. The output of D.C. offset correction is applied to both switches S2 107 and S1 111. It should be noted that switches as referred to in FIG. 4a and FIG. 4b are software switches and not hardware switches. The switches settings, referred to herein, are selected via a computer generated display. S2 107 will select whether the output of D.C. Offset Correction 105 will be applied to Line Filter 109. S1 determines if Raw Data File 113 should store the original data. Depending on the setting of S2 107, either line filtered or non-line filtered data will be applied to S4 115, S3 125 and to QRS Detection 117. QRS Detection 117 will determine the QRS position within the ECG signal. This QRS position will be used by the Arrhythmia Analysis Function 127 as well as the Average Heart Rate Display Calculation 149 and the Variable Delay 147.

Data input to S4 115 will have a choice of filtering options within the preferred embodiment. Included among these options is the Cubic Spine Method 123 well known to the art, a 0.05 Hz High Pass Filter (HPF) 121 and a 0.67 Hz HPF 119. The 0.67 Hz High Pass Filter (HPF) 119 employs a technique in filtering that is truly novel. It employs a bidirectional IIR filter to yield zero phase distortion using windowing techniques to eliminate ringing. The 0.67 Hz HPF 119 will be discussed in more detail below. After S4 115 has selected which filter, if any, is to be used, S5 133 will select a low pass filter that is to be used. The choices for low pass filters are 25 Hz LPF 135, 40 Hz LPF 137, 100 Hz LPF 139 or no low pass filter at all. The filtered ECG data output from the high pass and low pass filters is used by Template Matching 157 which also uses a Variable Delay 147 of the QRS position. The data output of the Template Matching Function 157 is used by Average Beat Calculation 159. After Average Beat Calculation 159, the output is used to generate the Average Beat Display 163, as well as being used to make ST Measurements 161 and is also used by the Average Beat Storage Logic 165 to retain a record of the Average Beat Calculation 159 in Average Beat File 167.

Figure 5:
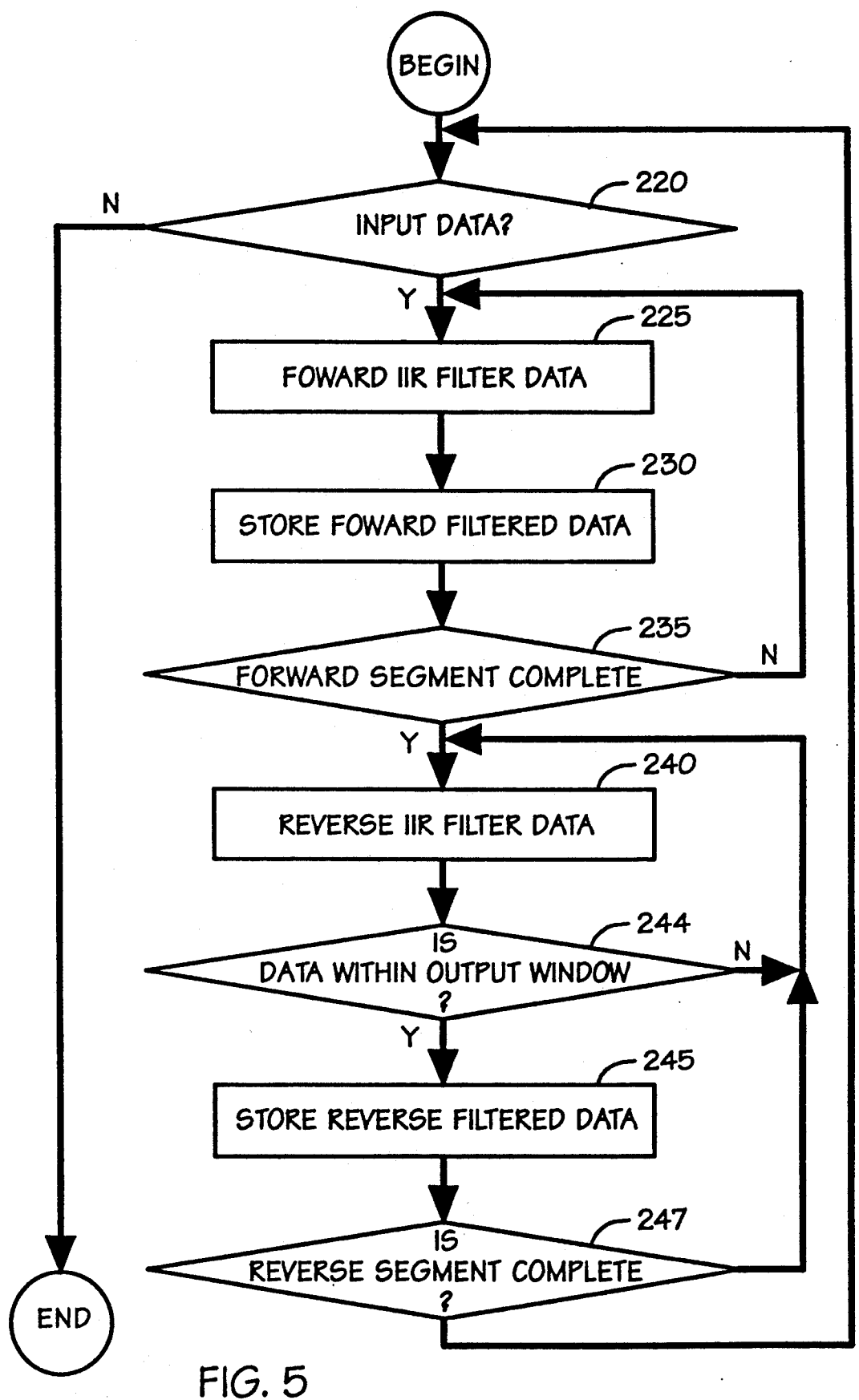
FIG. 5 is a flow diagram illustrating the generation of segments used in forming windows for the filtering techniques.

Data is digita,lly signal processed by CPU 40 in real time, using the algorithm shown in FIG. 5 for creating windows and for performing a bidirectional IIR on data within the windows.

Referring now to FIG. 5, the data flow diagram for the bidirectional filter, input data 220 reads digital data into the routine followed by forward filter 225 performing an IIR filtering pass over the data. Store forward data 230 holds this data while the computer 19 continually forward filters 225 data. The length of the forward filtering process is compared with a predetermined constant by forward segment complete 235 wherein the results yielding a true comparison indicates that the entire window length has been filtered. The data is then subjected to reverse filter 240 which begins at the end of the forward window and applies the filter in the reverse direction. Store reverse data 245 retains the results of reverse filter 240 only for those values that are going to be included in the final data tabulation. In the preferred embodiment, the terminal portion of each window is discarded. For this reason, this identical terminal portion of the reverse filtered data 240, is discarded and never combined with the forward filter data 225 results. Only the portion reverse filtered data 240 in that part of the window that will be retained is saved by store reverse filtered data 245. Reverse segment complete 247 determines when the window length is reached by comparison with a predetermined constant. Once analysis is complete, this condition is sensed by input data 220 returning false.

Within the confines of the FIG. 5, the present invention can operate in real time by judicious choice of window lengths, or if real time operation is not necessary increased window length can be obtained by usage of a 60 second buffer in which only a 2 second terminal portion would be discarded. This would leave a continuous 58 second window segment to be used in the final output. However, in the preferred embodiment real time operation is envisioned, and a three (3) second window is used with a two (2) second terminal portion that is discarded. Here, only one (1) of the three (3) seconds is used in the final output.

Figure 6:
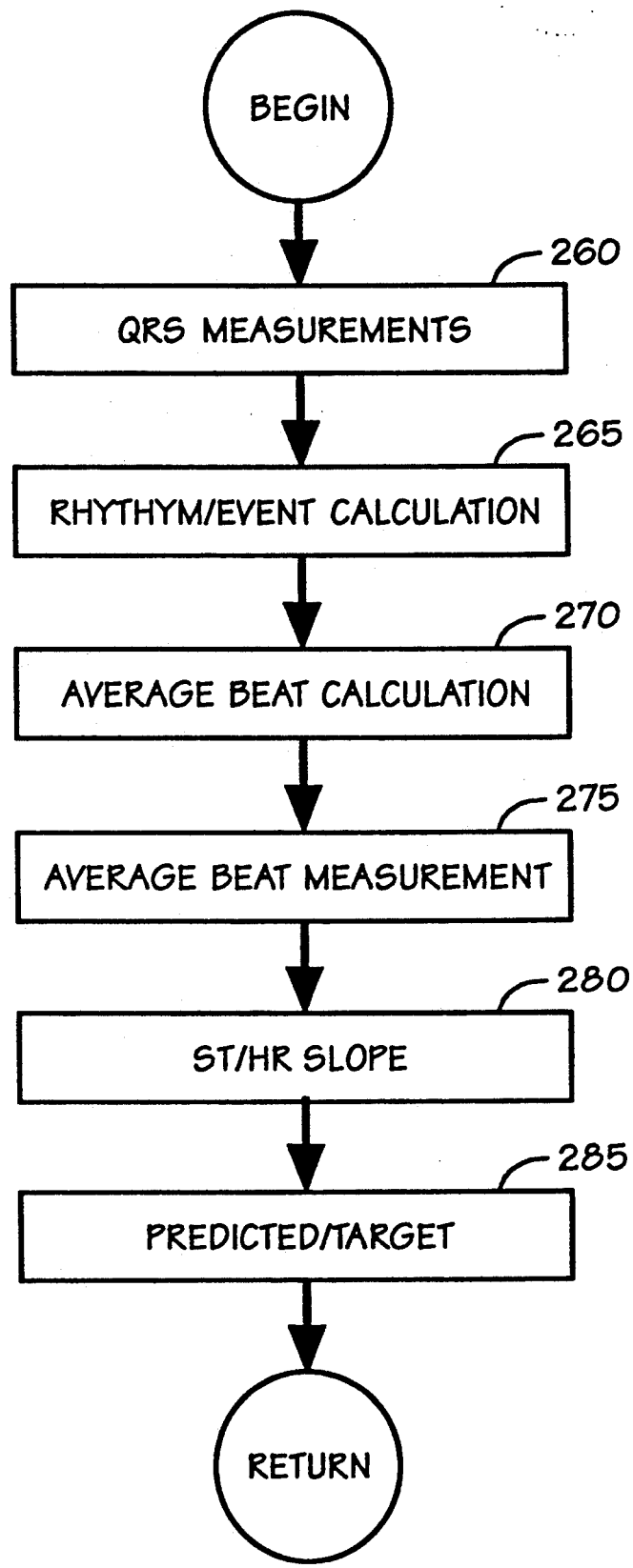
FIG. 6 is a flowchart showing the analysis steps.

Analysis on the filtered data is illustrated in FIG. 6 where a flow diagram of measurements and arrhythmia analysis can be seen. QRS Measurements 260 calculates and records information on a beat by beat basis. This information comprises time of occurrence of the beat, the R to R interval of previous beats and an average R to R interval. Beats are then given a classification label as being one of the following classes: (1) normal; (2) superventricular premature beat (atrial or nodal); (3) premature ventricular contraction; (4) ventricular escape beat; (5) beat of unknown origin; or (6) not QRS. Rhythm/Event Calculation 265 shall compute a value for instantaneous heart rate (IHR) as a function of the previous R to R interval and also calculate a value for average heart rate using the average R to R interval. Rhythm/Event Calculation 265 will then detect and record the arrhythmia events as detailed in Table 1 below. For each of these events the system shall store the start time and the end time of the event.

TABLE 1

| Number | Event Name | Meaning |
|---|---|---|
| 1 | Couplet | Two consecutive ventricular exsystol (VE) beats |
| 2 | Triplet | Three consecutive VE beats |
| 3 | Pause | Two beats where the R to R interval is longer > 2 sec. |
| 4 | Bigeminy | xVxVxV pattern where V is a Ve beat and x is not. |
| 5 | Trigeminy | xxVxxVxxV pattern where V is a VE beat and x is not. |
| 6 | Ventricular Tachycardia | Four or more consecutive VE beats. |
| 7 | Superventricular Tachycardia | Three or more consecutive beats intervals each 20% premature with a 3 beat avg. heat rate > = 80 bpm. |
| 8 | Bradycardia | Three or more consecutive beats at a rate lower than 45 bpm with the three most recent intervals greater than 1500 msec. |
| 9 | Average VE count per minute | A sliding window count of VE beats equal to 1 minute that is updated every second |

For each lead being analyzed in the system, the system shall perform average beat calculation. The system will then perform Average Beat Measurements 275 on all QRS's that have been updated by average beat 270 as follows: (1) ST level measurements; (2) ST slope measurements; (3) ST integral measurements; (4) ST index measurements; (5) QRS amplitude and duration measurements; (5) QRS amplitude and duration measurements; (6) Average R to R intervals; and (7) time of average beat calculation. ST/HR Slope Calculations 280 calculates for each average QRS stored in the system the average heart rate in beats per minute (bpm) and the ST level in millivolts. Predicted/Target 285 then figures the maximum heart rate that is targeted as being allowable according to age of the subject.

Figure 7:
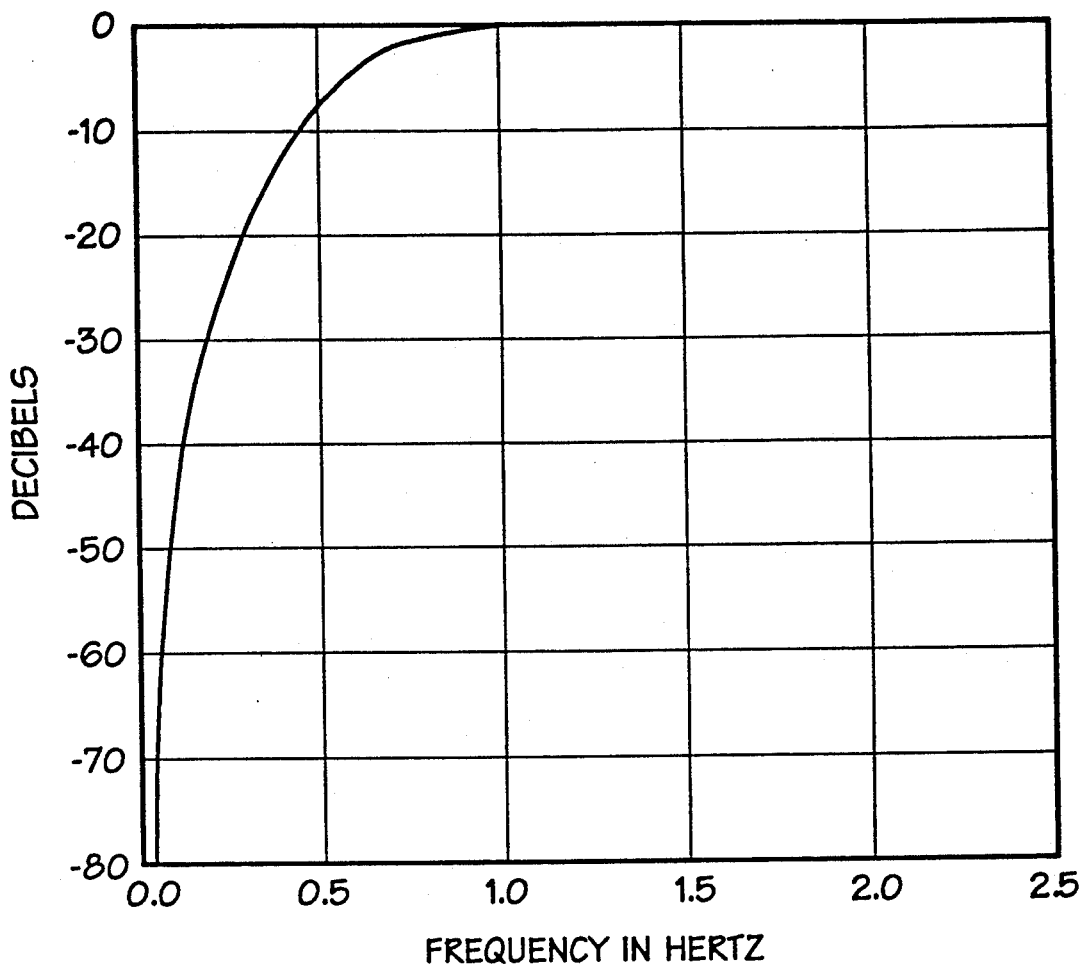
FIG. 7 is a frequency response diagram for a 3 pole butterworth filter.
Figure 8:
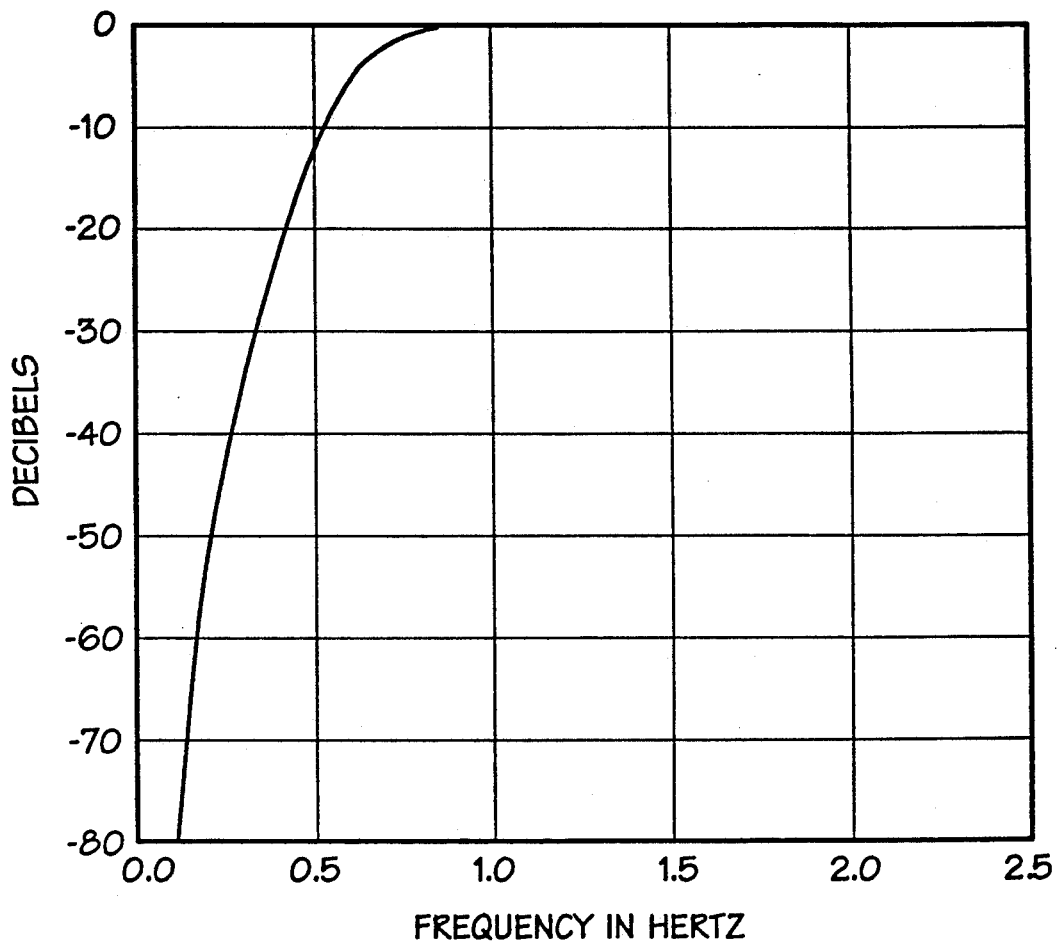
FIG. 8 is a frequency response diagram for a 5 pole butterworth filter.

Referring now to FIG. 7 which is the frequency response diagram for the 3-pole filter, and FIG. 8 which is the frequency response diagram for the 5 pole filter. These two basic filters both which are implementations of the analog butterworth filters, Will be described as used within the preferred embodiment. The Butterworth filters were selected because of its maximal flat frequency response in the pass band. Both a 3 pole and a 5 pole filter are considered. These two filters offer a trade-off between computational complexity, stop band attenuation, phase response and transient settling time.

A 3 pole butterworth filter can be described by equation 1 below.

$$H(s) = \frac{s}{s+1} \times \frac{s^2}{s^2 + s + 1} \quad \text{Equation 1.}$$

While the basic equation for a 5 pole butterworth filter is described by equation 2 as follows below.

$$H(s) = \frac{s}{s+1} \times \frac{s^2}{s^2 + 1.618s + 1} \times \frac{s^2}{s^2 + 0.618s + 1} \quad \text{Equation 2.}$$

These filters are normalized to a cut-off frequency of 1 radian per second and thus serve as general purpose templates for filtering designs.

The format of these filters can be generalized by cascading several first and second order filter sections. The general S domain transfer equation of the cascaded filter is as follows shown below as equation 3.

$$H(s) = \prod_{n=1}^{N} \left[ \frac{a_{2,n}s^2 + a_{1,n}s + a_{0,n}}{b_{2,n}s^2 + b_{1,n}s + b_{0,n}} \right] \quad \text{Equation 3.}$$

A third order (3 pole) filter may be obtained by cascading a one pole stage and a two pole stage. A fifth order filter (5 pole) may be obtained by cascading one single pole stage and two second order stages. A single stage may be constructed from a second order format shown in equation 3 by setting $a_{1,n}$, $a_{2,n}$ and $b_{2,n}$ to non-zero values. By using a bi-linear transform the above analog filters may be transformed into digital filters of form shown in the following equation 4:

$$H(s) = \prod_{n=1}^{N} \left[ \frac{1 + \alpha_{1,n}z^{-1} + \alpha_{2,n}z^{-2}}{1 + \beta_{1,n}z^{-1} + \beta_{2,n}z^{-2}} \right] \quad \text{Equation 4.}$$

A computer program can be used to calculate the bi-linear transform given specifications for the sampling frequency and the cut-off frequency. For this application the sampling frequency of 1,000 samples per second and the cut-off frequency is 0.67 hertz.

TABLE 2

| Coefficient | 3 pole Butterworth | 5 pole Butterworth |
|---|---|---|
| K | 0.9957991242 | 0.9932118058 |
| $\beta_{1,1}$ | 0.0042008981 | 0.0042008981 |
| $\beta_{2,1}$ | −0.9957991242 | −0.9957991242 |
| $\alpha_{1,1}$ | 0.0000000000 | 0.0000000000 |
| $\alpha_{2,1}$ | −1.0000000000 | −1.0000000000 |
| $\beta_{1,2}$ | −1.9957991242 | −1.9931941032 |
| $\beta_{2,2}$ | 0.9957991242 | 0.9932118058 |
| $\alpha_{1,2}$ | −2.0000000000 | −2.0000000000 |
| $\alpha_{2,2}$ | 1.0000000000 | 1.0000000000 |
| $\beta_{1,3}$ |  | −1.9973840714 |
| $\beta_{2,3}$ |  | 0.9974017739 |
| $\alpha_{1,3}$ |  | −2.0000000000 |
| $\alpha_{2,3}$ |  | −1.0000000000 |

Given the coefficient for the z domain transfer functions for the filters, it is possible to calculate the frequency response. FIG. 7 is the frequency response diagram for the 3-pole filter and FIG. 8 is the frequency response diagram for the 5 pole filter.

Figure 9:
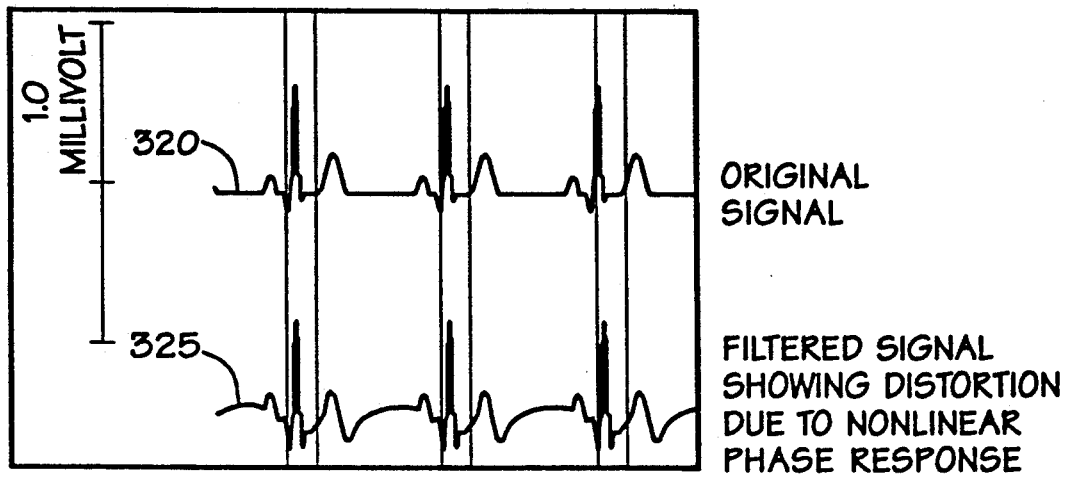
FIG. 9 is an illustration of the distortion that occurs in the ECG signal that has been filtered by a conventional 5-pole butterworth filter.

Although each of these filters yields a frequency response curve that is satisfactory for our purposes, these filters introduce significant noise distortions in the ECG due to the non-linear phase characteristics of the filter. FIG. 9 illustrates the distortions of the ECG due to application of the conventional 5-pole butterworth filter. The Upper Trace 320 is the unfiltered signal without noise, while the Lower Trace 325 is the filtered ECG signal. Because of the non-linear phase response, the frequency components of the ECG do not experience equal delays (phase angles) through the filter. This is the cause of the distortion shown in the bottom trace of FIG. 9.

Figure 10:
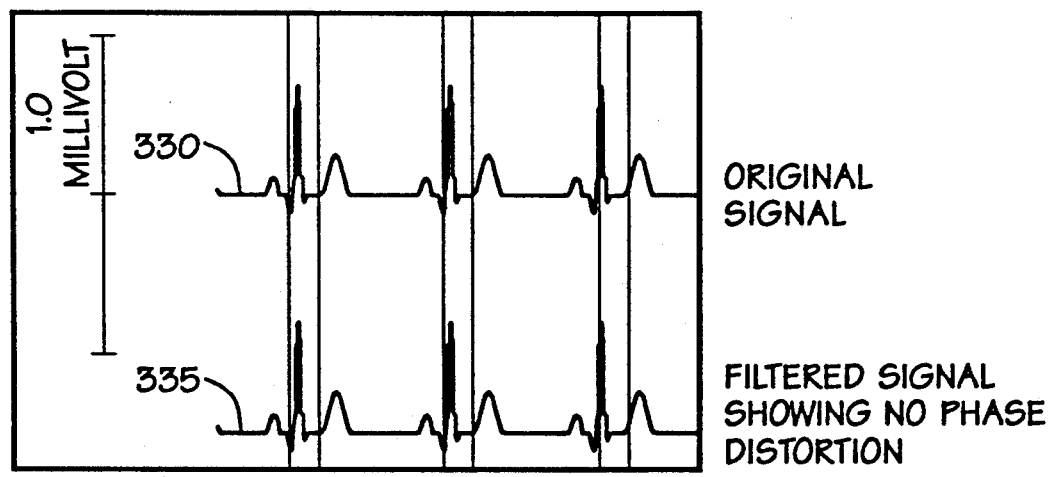
FIG. 10 represents the lack of distortion that results through the application of a 5-pole butterworth zero phase IIR filter on an ECG signal.

Referring now to FIG. 10, the result of implementing the solution to this problem is shown. By first applying the filter in a forward direction, and then applying the filter in a reverse direction, the phase distortions introduced into the signal by application of the filter in the forward direction are canceled out. The result in the signal has zero phase distortion and zero phase delay as shown in the Lower Trace 335 of FIG. 10. The added benefit of this approach is that the stop band attenuation is the square of the filters attenuation when applied in only one direction FIG. 10 presents the unfiltered signal and the signal after application of the 5-pole filter in a forward direction and then in the reverse direction. However, in the exercise stress testing environment such an implementation is not easily realized because signals must be analyzed and displayed in real time.

Figure 11:
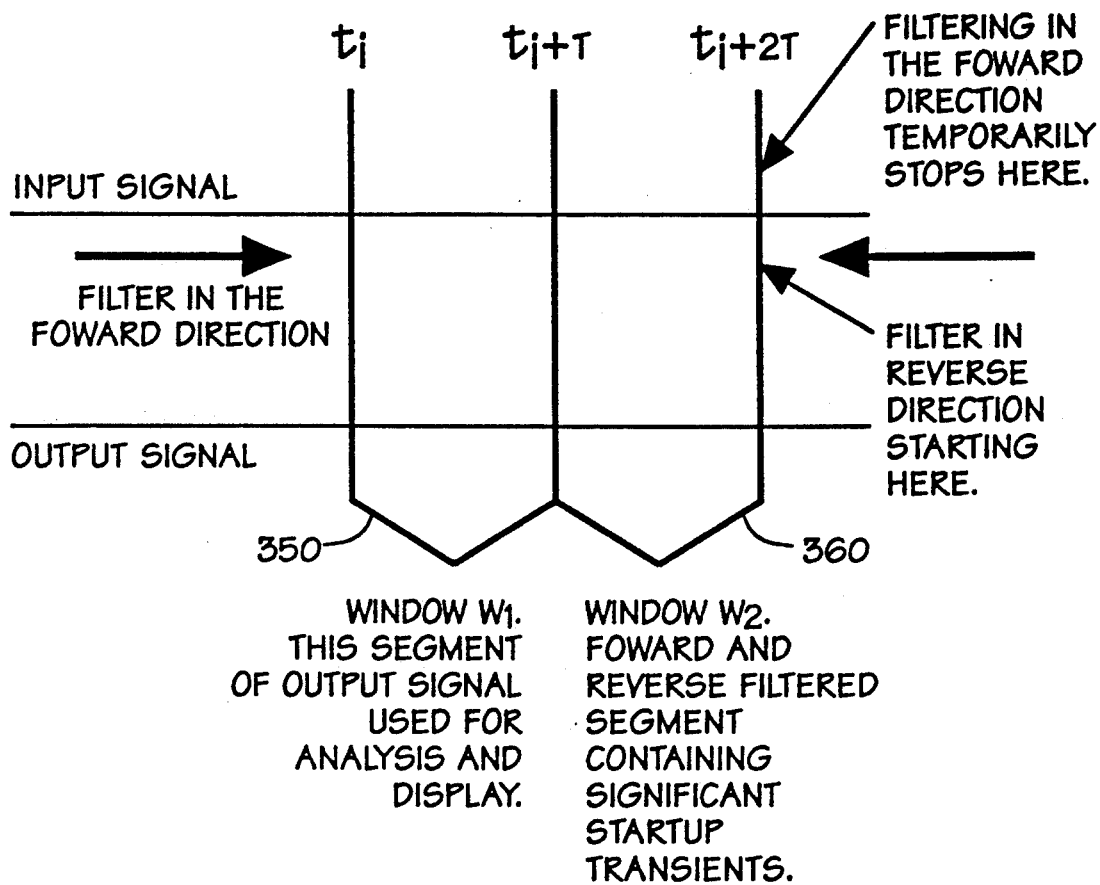
FIG. 11 illustrates windowing for bidirectional filtering.
Figure 12:
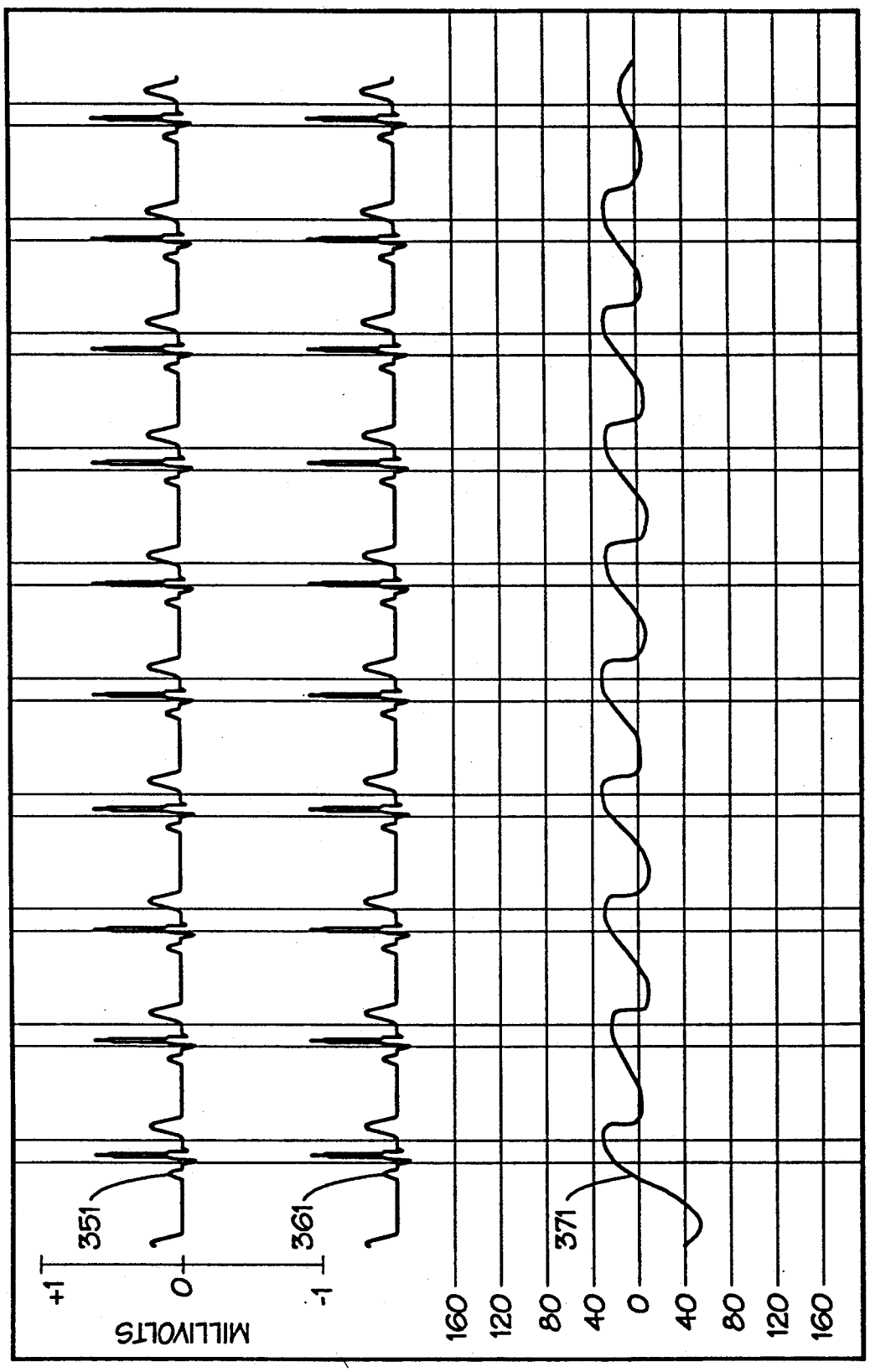
FIG. 12 is a diagram showing the input signal, output signal and error signal for a 5 pole butterworth filter with a 1.0 second window having a 60 bpm input.
Figure 13:
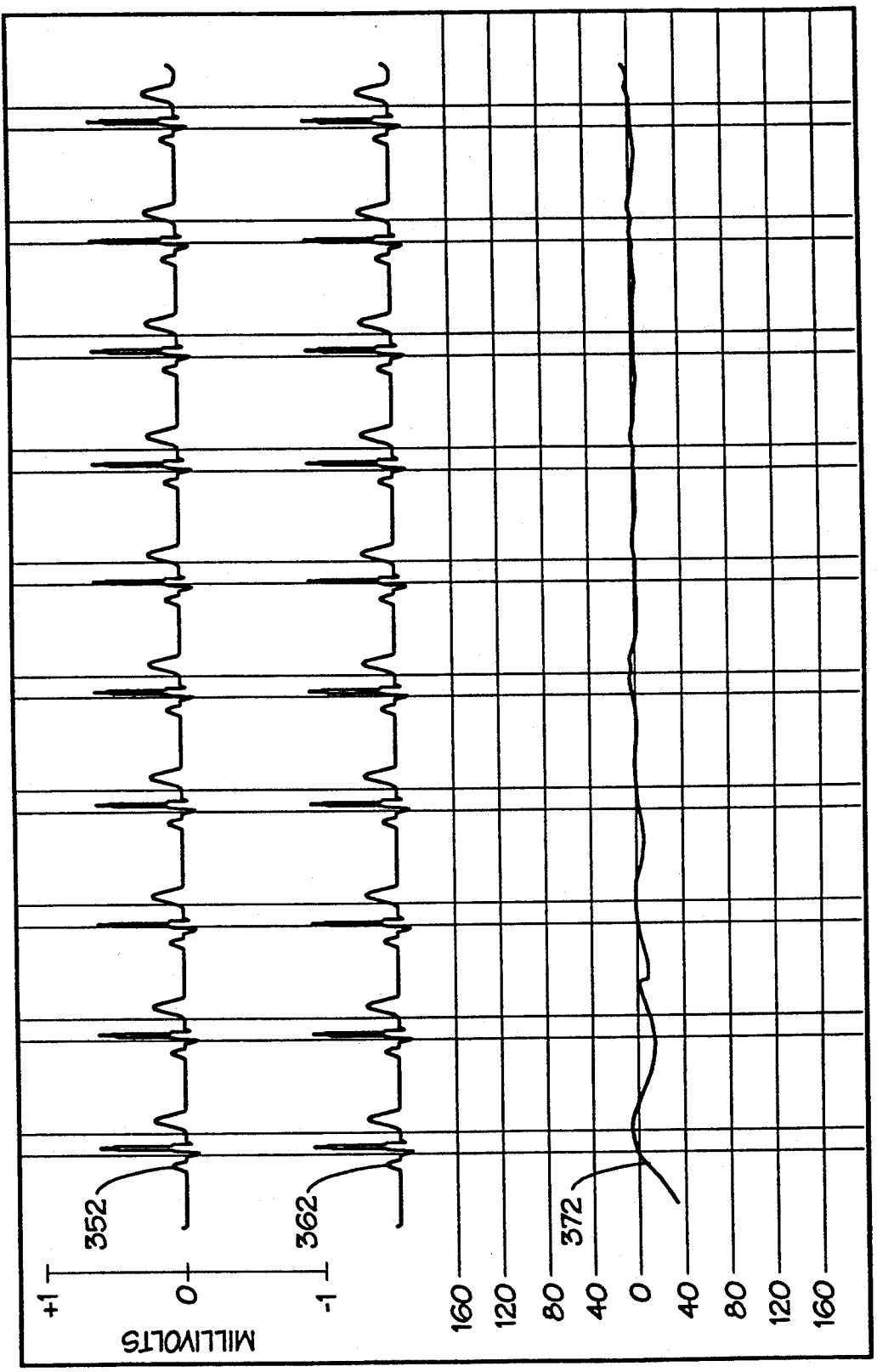
FIG. 13 is a diagram showing the input signal, output signal and error signal for a 5 pole butterworth filter with a 2.0 second window having a 60 bpm input.
Figure 14:
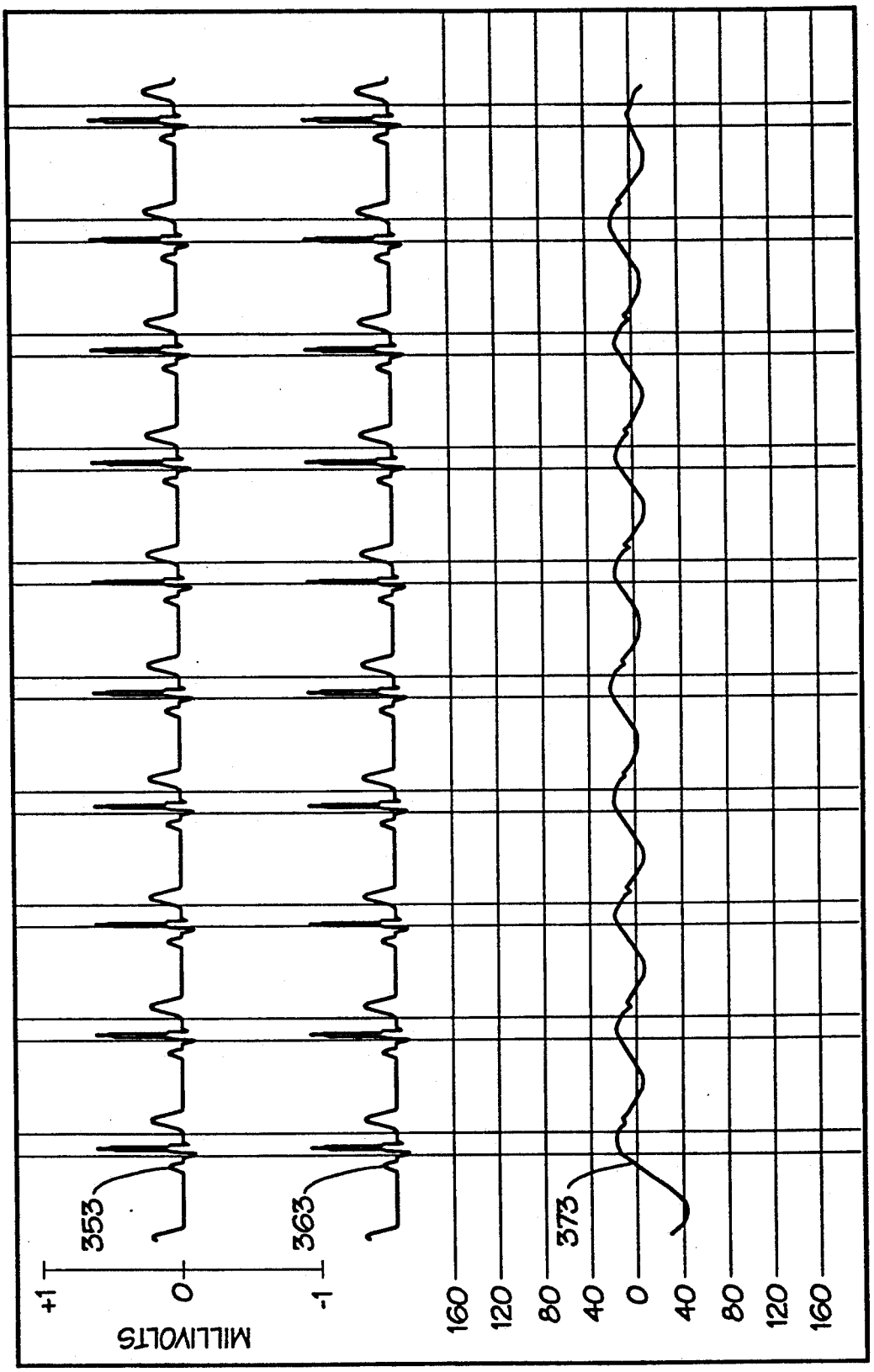
FIG. 14 is a diagram showing the input signal, output signal and error signal for a 3 pole butterworth filter with a 1.0 second window having a 60 bpm input.
Figure 15:
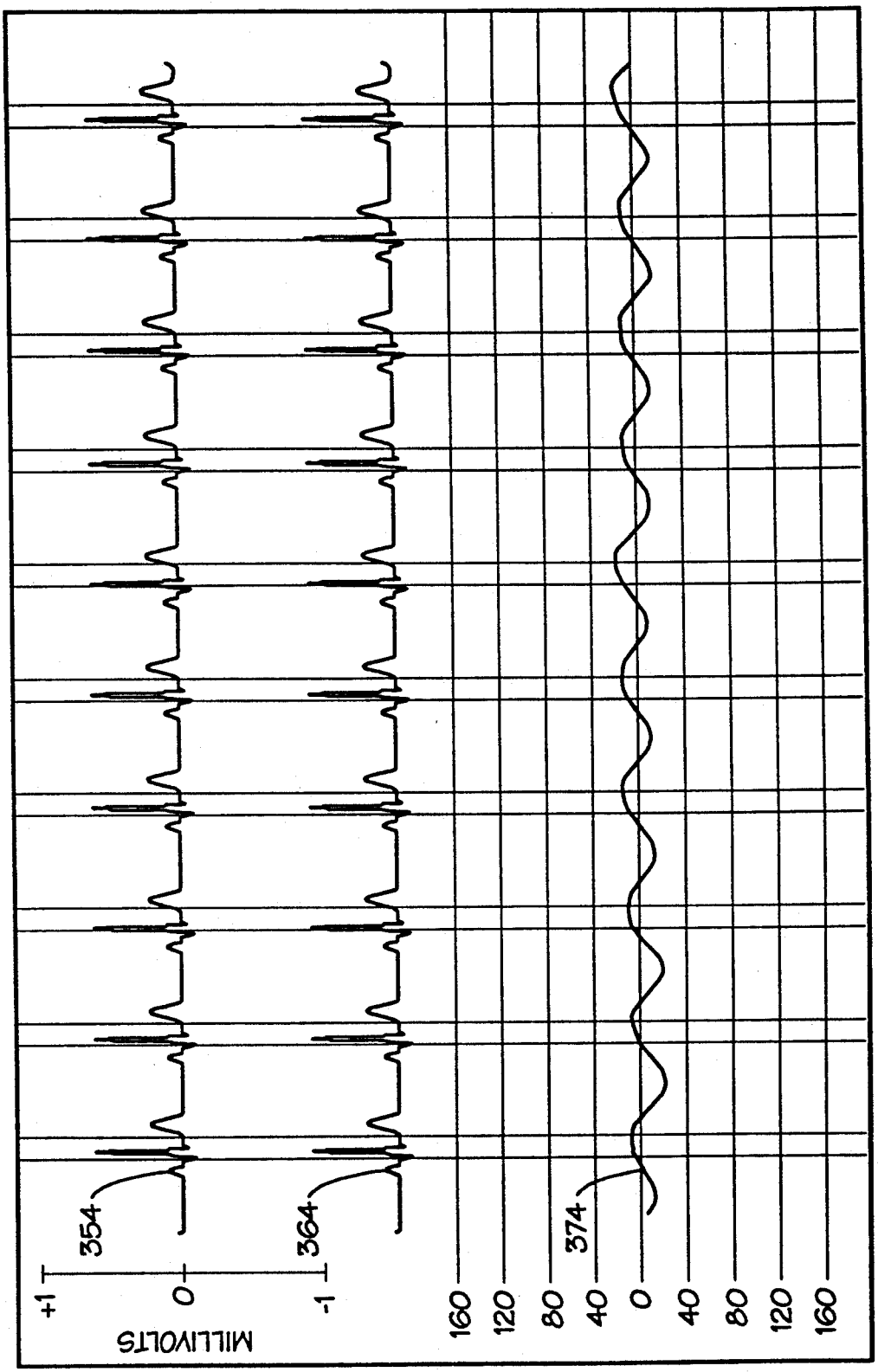
FIG. 15 is a diagram showing the input signal, output signal and error signal for a 3 pole butterworth filter with a 2.0 second window having a 60 bpm input.
Figure 16:
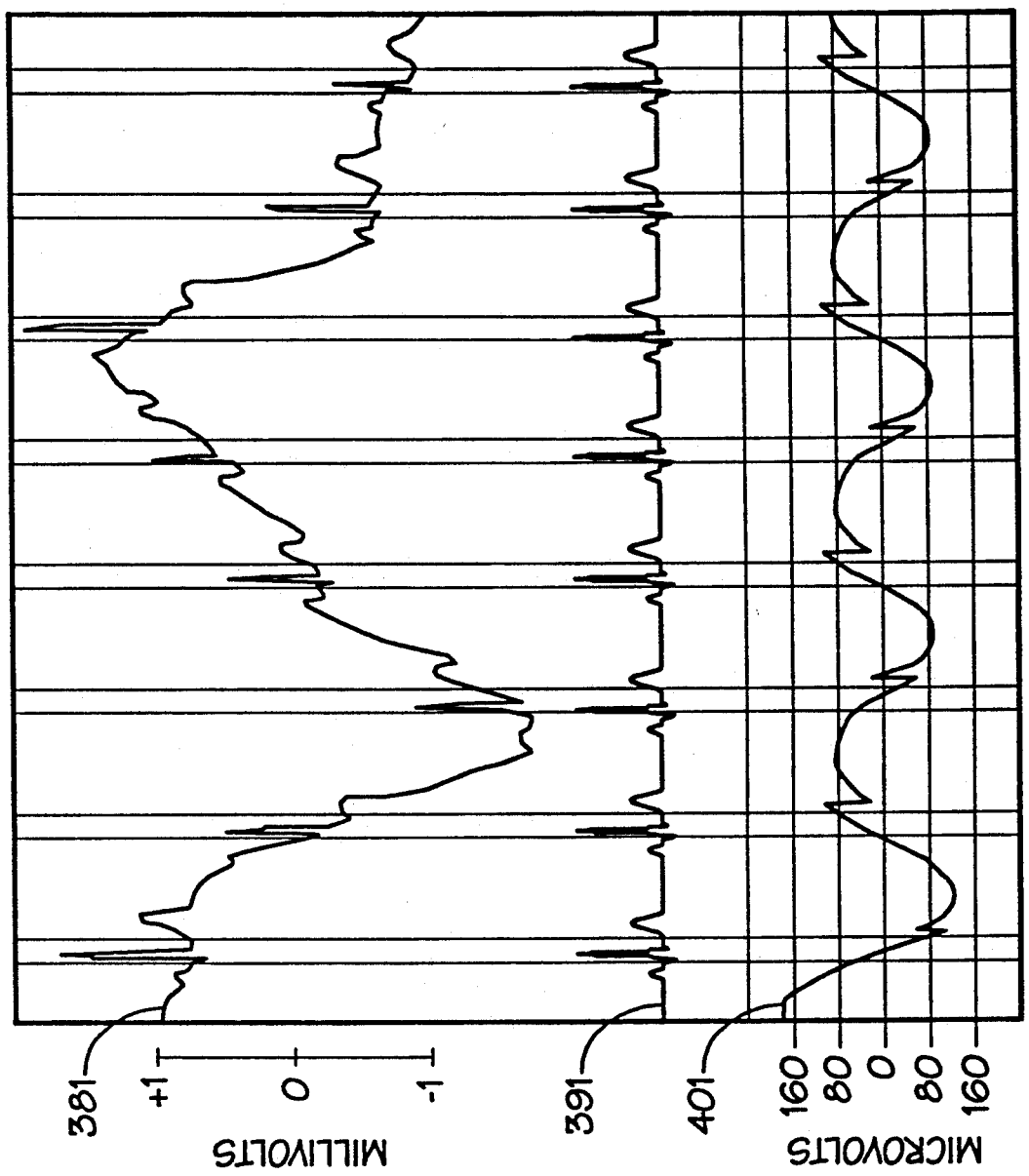
FIG. 16 is a diagram showing the input signal, output signal and error signal for a 5 pole butterworth filter with a 1.0 second window having a 60 bpm input containing baseline noise.
Figure 17:
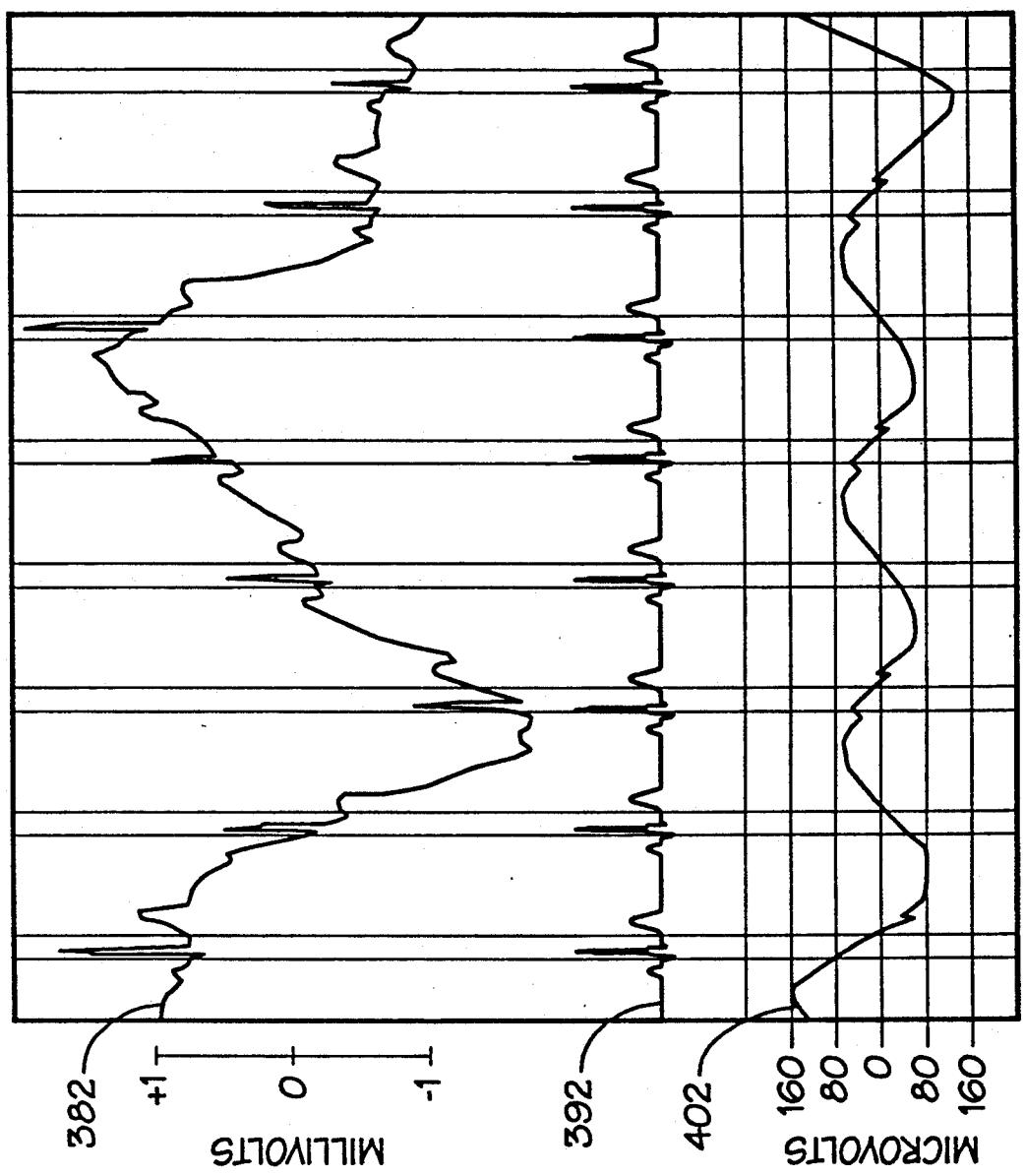
FIG. 17 is a diagram showing the input signal, output signal and error signal for a 5 pole butterworth filter with a 2.0 second window having a 60 bpm input containing baseline noise.
Figure 18:
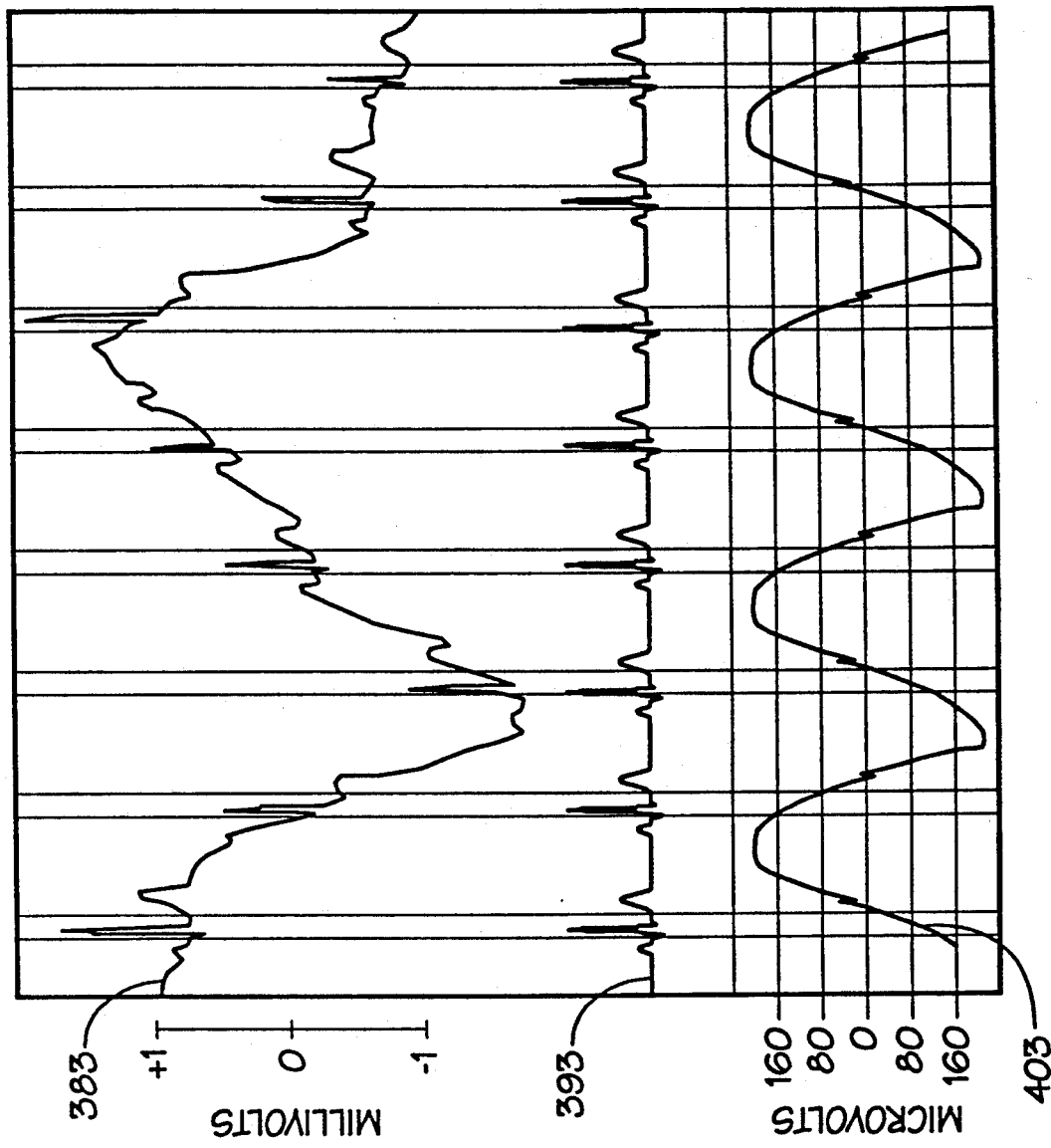
FIG. 18 is a diagram showing the input signal, output signal and error signal for a 3 pole butterworth filter with a 1.0 second window having a 60 bpm input containing baseline noise.
Figure 19:
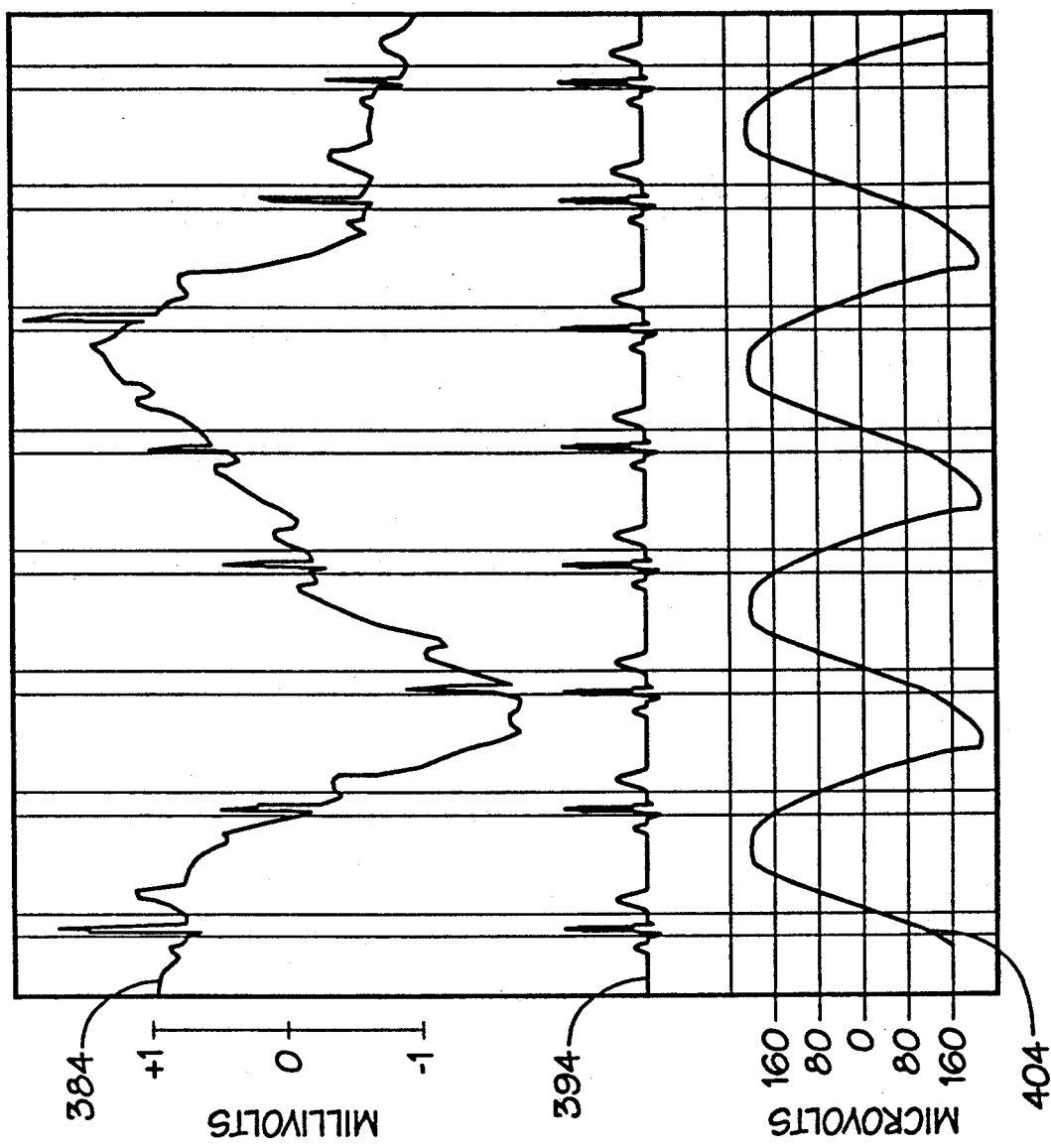
FIG. 19 is a diagram showing the input signal, output signal and error signal for a 3 pole butterworth filter with a 2.0 second window having a 60 bpm input containing baseline noise.

Referring now to FIG. 11, while filtering in both directions corrects the phase distortion problems, real time implementation of the zero phase IIR filter presents additional problems. The limited amount of time available in real time operation makes sequential filtering in a first forward direction and in a second reverse direction prohibitive using conventional filtering methods. The approach to the real time problem is to first filter in a forward direction over a predetermined window, and then to filter in a reverse direction starting at the end of the forward filtering window and ending at the starting position of the window. By discarding a terminal segment of this window, optimum results can be obtained. FIG. 11, which illustrates the windowing of data in an output signal of which T seconds is used for AN Analysis and Display Window 350. The output window is constructed by first filtering the input signal to time $t_{i+2T}$, in the forward direction, then stopping. The forward filtered signal is then filtered in the reverse direction from time $t_{i+2T}$ to time $t_i$ and the portion between $t_i$ and $t_{i+T}$ is copied into the output signal buffer and used for display and analysis. The portion of the bidirectional filtered signal between $t_{i+T}$ and $t_{i+2T}$ is discarded. The process is continued by shifting the windows by T seconds.

The output display and analysis window (hereinafter called $W_1$) 350. The window for establishing the history for the reverse time filter is $W_2$ 360 and is between times $T_{i+T}$ and $T_{i+2T}$. These two windows have been set equal for convenience, however, it is not necessary to set the length of $W_2$ equal to the length of the display and output window.

The input signal is filtered continuously in the forward direction so there are no start up transients due to filter initialization at window boundaries because the filter is already in the steady state. However, the reverse time filter will exhibit initialization transients due to the fact that the filter is initialized at time that $t_{i+2T}$, and there are no input values or history for the filter. Time $t_{i+2T}$ is actually time 0 for the reverse time filter.

Since the filter is being examined here are IIR filters, the amount of transients carried over into the output signal window will depend upon the window $W_2$, the type of filter used and the number of poles to the filter. These transients will introduce two types of distortions in the output signal. The first type of distortion is a general distortion of the output signal due to a spreading of the energy introduced by initialization of transients across the output window. This results in the window boundaries not joining together smoothly introducing steps into the output signal at the window boundaries, which is the second type of distortion. The magnitude of these errors are determined by the following: (1) The length of the reverse filtering window $W_2$ 360; (2) The settling time of the filter; (3) The stop band attenuation of the filter; and (4) The characteristics of the input signal.

The longer the $W_2$ 360 window, the less error introduced by the mismatch between windows because the reverse direction filter will have more time to settle. There is also a trade off between settling time with the filter and the stop band attenuation of the filter. High stop band attenuation tends to create a long transient settling time for the filter.

Referring now to FIG. 12 through FIG. 15 which are input, output, and error traces for 60 bpm input ECG signals that are free of drift. FIG. 12 through FIG. 15 all illustrate drift free input traces respectively 351, 352, 353 and 354 as well as acceptable output traces 361, 362, 363, and 364. The error traces are, respectively 371, 372, 373, and 374. The error trace shown in FIG. 13, for the 5 pole filter with a 2.0 window, indicates the least amount of error for any of the filters with a 60 bpm input. However, all of the error traces in FIG. 12 through FIG. 15 indicate acceptable error levels. It should be noted that the input and output traces (respectively 351, 352, 363, 354 and 361, 362, 363, 364) in FIG. 12 through FIG. 15 are shown on a millivolt scale while the error traces in FIG. 12 through FIG. 15 (respectfully 371, 372, 373 and 374) are displayed on a microvolt scale. In this manner the error can be seen.

The following table presents results of tests achieved using unfiltered and filtered signals having the two filters each tested with different window widths. The following table illustrates the figures and samples taken from both 5 and 3 pole filters with window widths of 1.0 and 2.0 seconds for ECG with a heart rate of 60 BPM with essentially no drift in the input signal.

TABLE 3

| | | Figures for Window Width for Clean Signals | | | | |
|---|---|---|---|---|---|---|
| Number Poles | Window Width | Heart Rate | ST Depression | Noise Added | Figure Number | DISTORTION COMMENTS |
| 5 | 1.0 sec. | 60 BPM | 0.0 mm | no | 13 | Sine wave distortion with steps |
| 5 | 2.0 sec. | 60 BPM | 0.0 mm | no | 14 | Little or no filter error |
| 3 | 1.0 sec. | 60 BPM | 0.0 mm | no | 15 | Sine wave distortion |
| 3 | 2.0 sec. | 60 BPM | 0.0 mm | no | 16 | Sine wave distortion |

The error signal for the 5 pole filter with a window of 1.0 seconds shows quite a lot of error. This error is primarily due to the fact that the window width is too short and the filter did not have enough time to settle in the reverse direction. These sharp discontinuities or steps in the air signal are due to the fact that the output windows do not match perfectly.

The signal with the 5 pole filter using a 2.0 second window, with the exception of the start up transients, showed very little noise in the signal. The error of each QRS window varies between 3.75 and 6.25 microvolts which is probably due to noise within the input signal. The application of the 3 pole filter using a 1.0 second window shows only a slight discontinuity in the error signal due to the windowing. The overall peak to peak noise that resembles a sine wave is due to the 1.0 Hz of the input signal due to the QRS. The 1.0 Hz frequency is sufficiently close to the 0.67 Hz cut off frequency (−3DB.) as to be slightly attenuated. The error of the 3 pole filter using a 2.0 second window is significantly less. Notice that there is no observable step or discontinuity in the filtered signal.

There are several characteristics within the input ECG signal that will affect the amount of noise introduced by the filter windowing technique. The heart rate, amount of ST depression and the amount of drift and sudden rate changes will affect the output signal. The attenuation of the ECG baseline noise due to preselected drift frequencies was compared with the 3 pole and 5 pole filters each having a 1.0 second and a 2.0 second window. Table 4 below lists the data from FIG. 16 through FIG. 19. The following noise signal was added to the input signal.

$$N_i = 1000\sin(\Omega_1 * i) + 3000\sin(\Omega_2 * i) \qquad \text{Equation 5}$$

where $$\Omega_1 = \frac{(2*\pi*0.5)}{f_s}$$

and $$\Omega_2 = \frac{(2*n*0.2)}{f_s}$$

The term $f_s$ is the sampling frequency and is equal to 1,000 samples per second. Hence the digital equivalent of 0.5 hertz signal was summed with a 0.2 hertz signal to generate baseline noise. This baseline noise factor makes a significant comparison with the 60 bpm input. At 60 bpm the heart rate is a 1 Hz signal, just above the 0.67 Hz cutoff. The 0.5 Hz element of the baseline noise now added creates a signal input below the 0.67 Hz cutoff but still close to the cutoff point. These two factors contribute to create what is essentially a worst case scenario for the filter, e.g. signal inputs close to the cutoff value. As can be in FIG. 16 through FIG. 19, the resulting error (as measured in microvolts) is clearly an acceptable level.

Table 4 below lists the results of data that can be seen in the waveforms show in FIG. 16 through FIG. 19.

TABLE 4

| | | .2 Hz and .5 Hz drift inserted into ECG Input | | | | |
|---|---|---|---|---|---|---|
| Number Poles | Window Width | Heart Rate | ST Depression | Noise Added | Figure Number | DISTORTION COMMENTS |
| 5 | 1.0 sec. | 60 BPM | 0.0 mm | yes | 17 | Large steps |
| 5 | 2.0 sec. | 60 BPM | 0.0 mm | yes | 18 | Small steps |
| 3 | 1.0 sec. | 60 BPM | 0.0 mm | yes | 19 | Moderate |
| 3 | 2.0 sec. | 60 BPM | 0.0 mm | yes | 20 | No steps |

The inputs signals (381, 382, 383, and 384) in FIG. 16 through FIG. 19 and the output signals (391, 392, 393 and 394) are shown on a millivolt scale. As can be seen the input signals 381, 382, 383, and 384 exhibit a large amount of drift which are basically not seen in the output signals 391, 392, 393 and 394. The error traces (401, 402, 403, and 404) are shown on a microvolt scale and are actually a thousand times smaller than appears relative to the input traces 381, 382, 383 and 384 and the output traces 391, 392, 393 and 394 on FIG. 16 though FIG. 19.

The 5 pole filter with a 1.0 second window exhibits the largest discontinuities with steps on the order of 80 micro volts or so near the center of the signal (steady state). The same filter with the 2.0 second window will show steps in the error signal but they are significantly smaller than those in the 1.0 second window, and still significantly smaller than the remaining noise in the signal. The 3 pole filter with the 1.0 second window exhibits steps in the error signal, but the same filter with the 2.0 second window shows no discontinuities in the error signal.

The table below summarizes the performance of the two filters.

TABLE 5

| No. Filter Poles | Window Width | Approx P-P Error | Approx Attenuation | Approx. QRS Window Error |
|---|---|---|---|---|
| 5 | 1.0 | 188 μvolts | 24 db. | 70–80 μvolts |
| 5 | 2.0 | 136 μvolts | 27 db. | 45–55 μvolts |
| 3 | 1.0 | 350 μvolts | 18 db. | 100–200 μV |
| 3 | 2.0 | 367 μvolts | 18 db. | 60–100 μV |

The 5 pole filter with a 2.0 second window has the best performance in terms of attenuation and QRS error period. The 3 pole filter does not straighten the baseline as much as the 5 pole filter, but its performance with a large amount of baseline noise is not unacceptable. Filter error at high, medium and very low heart rates versus filter type and window width were studied. As expected, both filters introduce little or no noise at heart rates of 120 and 240 BPM. At 30 BPM however, the baseline exhibits its drift. This drift is due to the fact that the frequency of the heart rate is well within the cut off region of the filters. The 5 pole and the 3 pole filters exhibit about the same amount of control of peak to peak baseline error. QRS errors appear to be exceptionally low. The length of the window does not appear to affect the amount of error introduced by the filters or these heart rates.

Errors and response to rapid changes in the heart rate were tested versus the type of filter. The heart rate was changed instantaneously from 60 BPM to 120 BPM. Only a 2.0 second window was used for both three and five pole filters. Both filters displayed a fairly sudden increase in the peak to peak error when the heart rate changes suddenly. This error is on the order of 100–120 microvolts for both filters. Even though the peak to peak baseline error is high, both filters have a QRS window error on the order of 40–50 micro volts. The largest error occurred in the first QRS at which the rate change occurred. The error disappeared from the signal after that.

Filter error was tested for a deep ST depression for the two filter types and window widths. QRS components with the ST depression of approximately 3.5 millimeters of depression were filtered with both filters using the 1.0 second and the 2.0 second windows. The 5-pole filter with the 1.0 second window exhibits large discontinuities with a peak to peak magnitude of approximately 60 micro volts. The 5 pole filter with a 2.0 second window had the best over all performance.

Filter error for a change in ST depression versus filter type and window width was tested by introducing a step change of 1.0 mm into the ECG for each of the four filter and window combinations discussed above. All filter/window combinations exhibited a deflection in the baseline error signal of approximately 80 micro volts. As this is a rather low frequency range, the QRS window errors were quite low in all cases.

CONCLUSIONS

In review of the response of the 5 pole high pass filter and 3 pole high pass filter with windows of 1.0 seconds and 2.0 seconds, the following conclusions have been reached:

(1) The 5 pole filter with a 2.0 second window provides the best attenuation with only a very small discontinuities at window boundaries. The largest filter has the advantage of a greatly superior attenuation, it has the disadvantages of the total signal delay of 4.0 seconds.

(2) The 3 pole filter with a 1.0 second window offers less attenuation with acceptable errors at window boundaries. This filter has the advantage of a much shorter signal delay of 2.0 seconds.

Another implementation that uses a 5 pole filter having an output window, $W_1$, of 1 second and a second window, $W_2$, of 2 seconds has also been studied. It was found that this design produces results identical to the 5 pole filter with $W_1$ and $W_2$ both equal to 2 seconds. The advantage of this filter is that it has a delay of only 3 seconds and still has the higher stop band attenuation. This approach seems to offer the best performance for the design compromises made.

Although a Butterworth filter provides the best compromise filter design, the present invention is not limited thereto, and moreover, designs implementing filters within fewer or greater number of poles are also applicable. Other filters, such as Bessel Filters, may be used in place of the design employing the Butterworth filter. The Bessel filter has the advantage of providing a design containing less overshoot in response to impulse signals and the disadvantage of providing less attenuation in the stop band.

The inventor envisions that the generic properties of the present invention have numerous applications and, while the best mode known to the inventor is disclosed in detail herein, sufficient disclosure is made to enable persons skilled within the arts of stress testing and digital signal processing to employ the invention towards other embodiments which are but obvious improvement over the disclosure of the present invention. These obvious variations would not, therefore, depart from the spirit and scope of the invention as defined in the appended claims.

I claim:

1. A stress test system for eliminating noise contained in an accelerated ECG signal comprising:

electrode means for detecting bioelectric signals generated by accelerated hearts of human subjects and generating, therefrom, an analog electrical signal;

digitizing means for converting said analog signal into a series of digital signals;

processing means for performing digital processing on said series of digital signals;

storage means operatively coupled to said processing means for storing data relating to said processing means operation, including storage of a predetermined length;

segmentation means contained within said processing means for dividing said series of digital signals into a series of windows, each of said windows being of said predetermined length;

filtering means contained within said processing means, said filtering means performing a bidirectional infinite impulse response (IIR) filter upon each of said windows; and comparison means contained within said processing means for determining when said filtering means has completed each pass of said bidirectional IIR filter by comparing the length filtered in each direction against said predetermined length.

2. The invention defined by claim 1 further comprising:

analytical means contained within said processing means, said analytical means performing an analysis on said electrical signal after said filtering means performs said bidirectional IIR upon each of said windows; and means responsive to said analytical means for indicating a result of said digital analysis.

3. The invention of claim 1 wherein said filtering means performs said bidirectional IIR filter in a first direction over each of said windows of detected ECG signals, and in a second direction opposite to said first direction over each of said windows, thereby canceling out any resulting phase distortions occurring fromn employing said IIR in said first direction.

4. The invention of claim 3 wherein said window has a terminal portion relative to said first direction that is discarded by said filtering means.

5. The invention of claim 3 wherein said window is approximately 3 seconds long.

6. The invention of claim 5 wherein said terminal portion is approximately 2 seconds long.

7. The invention of claim 3 wherein said filtering means is a butterworth filter.

8. The invention of claim 7 wherein said butterworth filter is a 3 pole filter.

9. The invention of claim 7 wherein said butterworth filter is a 5 pole filter.

10. A system for filtering electrocardiographic signals generated as a result of accelerated cardiac activity comprising:

at least one electrocardiographic sensor capable of detecting bioelectric signals generated by accelerated hearts of human subjects, said sensor being attached to human subjects to detect heartbeats, and generate an analog electrical signal, therefrom;

digitizing means for converting said analog electrical signal into a series of digital electrical signals;

computational means for dividing said series of digital electrical signals into a series of segments each of said segments having a predetermined length;

filtering means contained within said computational means, for performing a zero phase bidirectional infinite impulse response (IIR) filter on said series of segments; and means responsive to said filtering means for reconstructing said series of segments to create an estimated baseline level of said analog signal.

11. The invention defined by claim 10 further comprising comparison means for determining that said bidirectional IIR filter has filtered said digitized electrical over a length equal to said predetermined length for each direction of operation for said bidirectional filter.

12. The invention of claim 10 wherein said filtering means performs said bidirectional IIR in a first direction over said predetermined length of detected ECG signals, and in a second direction that is opposite said first direction over said predetermined length thereby canceling out any resulting phase distortions occurring from employing said IIR in said first direction.

13. The invention of claim 12 wherein said predetermined length has a first portion and a second portion, selected such that one of said portions may be discarded to eliminate ringing generated by said IIR filter.

14. The invention of claim 12 wherein said IIR filter is a butterworth filter.

* * * * *